United States Patent [19]

Orlowski et al.

[11] Patent Number: 4,648,845

[45] Date of Patent: Mar. 10, 1987

[54] METHOD FOR REPAIRING OF VENEERED DENTAL CAST RESTORATION

[75] Inventors: Jan A. Orlowski, Altadena; David V. Butler, West Covina, both of Calif.

[73] Assignee: Scientific Pharmaceuticals, Inc., Duarate, Calif.

[21] Appl. No.: 802,326

[22] Filed: Nov. 27, 1985

[51] Int. Cl.$^4$ .......................... A61C 5/00; A61K 6/08
[52] U.S. Cl. .................................. 433/217.1; 427/2; 523/115; 523/116
[58] Field of Search ............... 433/217.1; 523/115, 523/116, 117; 427/2

[56] References Cited

U.S. PATENT DOCUMENTS 4,150,485  4/1979  Lee et al. ........................... 523/220
4,548,689  10/1985  Sakashita et al. .................. 523/116

*Primary Examiner*—Lorenzo B. Hayes
*Attorney, Agent, or Firm*—Cushman, Darby & Cushman

[57] ABSTRACT

There is provided a method for indirect bonding of chemically or light curable resin based restoratives especially acrylates and methacrylates, to the metal base of dental cast restorations. The invention is particularly useful in cases of in situ repairs of damaged or worn porcelain or polymeric veneers on cast restorations made of precious and non-precious metals. According to the invention, the exposed metal of the restoration is covered with a layer of primer consisting essentially of a copolymer of polymethacrylic or polyacrylic acid followed by the application of the polymerizable restorative material.

21 Claims, No Drawings

METHOD FOR REPAIRING OF VENEERED DENTAL CAST RESTORATION

FIELD OF THE INVENTION

This invention concerns the use of a water insoluble copolymer of polyacrylic or polymethacrylic acid as a primer for enhancing bonding strength between the metal base of the restoration and the polymerizable restorative material, used for re-veneering of the damaged or worn parts of the restoration.

The primer is preferably in the form of a solution of the film forming polyacrylic or polymethacrylic acid based resin in a volatile solvent. The restorative material is preferably in the form of a polymerizable methacrylic or acrylic resin or blends thereof containing one to four methacrylate groups per molecule, tooth colored and containing a fine vitreous filler. The restorative may be of the chemically or light (UV or visible) initiated curing system type. The primer acts as a bridge between the metal base, usually made of gold, palladium or nickel alloys, and the restorative material. It provides good bonding strength between these materials allowing for successful and durable in situ repairs of veneers on cast restorations.

BACKGROUND OF THE INVENTION

Progress made in the field of prosthetic denistry during the last century, combined with constantly increasing longevity of the population and the rise in the standard of living, have contributed greatly to the popularity and increased utilization of permanent dental prothesis. With this came the need for a cost effective, esthetically acceptable and reliable method for restoring fractured or worn veneers made of porcelain or acrylic.type resins. These materials are more fragile and/or softer than the durable metal base of the cast restoration. Therefore, they are more susceptible to fracture and/or wear.

The in situ repair of damaged or worn restorations was, up to now, virtually impossible. applying a layer consisting of a copolymer of acrylic or methacrylic acid and a copolymerizable monomer over the metal base of the restoration, followed by the application of a conventional resih based dental restorative. The intermediate layer provides good bonding strength, both to metal and restoratives, thus assuring durability of the restoration. Illustrative resin based dental restoratives are set forth in Lee U.S. Pat. No. 4,107,845, Waknine U.S. Pat. No. 4,544,359, Waknine U.S. Pat. No. 4,547,531, and Bowen U.S. Pat. No. 3,066,112. The entire disclosures of these patents are hereby incorporated by reference and relied upon.

By copolymerizing acrylic or methacrylic acid with another monomer, insolubility in oral fluids is achieved, while preserving the good adhesive properties of polyacids. The presence of ethylenically unsaturated groups in the primer, combined with its limited chemical resistance to acrylic or methacrylic resins (present in the restorative) assures a good bond between the primer and the restorative, enhanced by the copolymerization in the interface layer.

SUMMARY OF THE INVENTION

Conventional permanent dental prothestic restorations, such as crowns and bridges, are most commonly composed of a cast metal base and porcelain or acrylic veneer. Precious and non-precious metals, used for making cast restorations, include gold, palladium, silver and nickel alloys, stainless steel, etc. The porcelain veneers are relatively resistant to wear but susceptible to mechanical damage, because of the brittleness of the material. The acrylic veneers are less likely to chip or break, but are likely to wear.

The need for an effective and durable repair method is well recognized by the dental profession. For economic, as well as for convenience reasons, such repairs should be made in situ; without removing the restoration from the mouth.

Especially difficult to repair are cases where, due to fracture or wear, a substantial area of metal is exposed. The success of the restoration procedure depends on, among other factors, a bonding force between a restorative repair material and a metal base. For reasons of esthetics and wear resistance the material of choice for making such repairs should be a filled acrylic or methacrylic resin of a suitable consistency. Materials of this type are commonly used in denistry for filling cavities and for resurfacing deficient enamel; they are known under the name of composite restoratives. Illustrative examples of such restorative materials are set forth in the four above-mentioned U.S. patents.

Unfortunately, composite restoratives do not exhibit good adhesive properties when applied on metals in general, and on glues and its alloys in particular. Attempts to increase the bonding strength by roughening the exposed surface of the metal did not bring improvement significant enough to assure durable restorations. The epoxy type resins, used as metal primers, did not provide adequate bonding strength; moreover, these resins are susceptible to deterioration in moist environments. Cyanoacrylate glues have also been proven ineffective for the reason of susceptability to deterioration in oral conditions. Some manufacturers have recommended the use of organofunctional silane primers for repairing damaged porcelain veneers. These primers, while improving bonding to porcelain, did not contribute to bonding to metal. Therefore, they are virtually useless in clinical situations where relatively large surfaces of metal are exposed.

The method of repairing veneers, according to this invention, employs a novel primer consisting of, or consisting essentially of, a copolymer of acrylic or methacrylic acid, preferably with a methacrylate or acrylate ester. Such primer has been found to provide a strong bond to metal bases as well as to restoratives. The primer is preferably applied on metal in the form of a solution in a volatile solvent. The solvent is allowed to evaporate, leaving a layer of the polymeric primer on the surface. The primer itself may be formulated in the following forms:

1. As a polymerizable light or self-cured mixture of acrylic, methacrylic, polyacrylic, or polymethacrylic acids with an acrylate or methacrylate ester.
2. As a copolymer of acrylic or methacrylic acid with an acrylate or methacrylate ester.
3. As a polymerizable mixture of a copolymer or copolymers described in 2 above with an acrylate or methacrylate ester.

The acrylate and/or methacrylate ester portion of the polymerizable mixture can be 1 to 50%, preferably 5 to 25% of the total of (1) acrylate and/or methacrylate ester and (2) acrylic acid and/or methacrylic acid. When a cross-linking agent is present, e.g., a diacrylate or methacrylate, it should be present preferably in an amount of not over 10%.

The acid number of the mixture (1), (2), or (3) should at least 20, preferably above 65, most desirable range being 80 to 120.

Unless otherwise indicated, all parts and percentages are by weight.

The method can comprise, consist essentially of, or consist of the stated steps with the recited materials.

In order to facilitate application, it is desirable that a volatile solvent is used as a carrier for the above-described resins The solvent should have the following characteristics:

1. It should exhibit a fast rate of evaporation at body temperature.
2. It should be biologically acceptable.
3. It should not interfere with the adhesive properties of the primer.

After evaporation of the solvent, the polymeric layer may be further polymerized, by chemical means, or by ultra-violet or visible light.

Methacrylic and acrylic acids or their homo- and copolymers, used in the primer formulations according to this invention, have molecular weights, prior to curing, of no more than 1,000,000, preferably no more than 400,000.

Non-limiting examples of mono-acrylate or mono-methacrylate copolymerizing monomers (or polymers thereof) used in formulations according to this invention are: phenyl-, cyclohexyl-, lower alkyl ($C_1$–$C_6$)-, glycidyl-, hydroxyalkyl ($C_2$–$C_4$)-, chloroalkyl ($C_1$–$C_6$)-, alkoxy-alkyl ($C_1$–$C_4$)-, furfuryl, tetrahydrofurfuryl and vinyl acrylates or methacrylates. Specific esters are phenyl acrylate, phenyl methacrylate, methyl acrylate, methyl methacrylate, ethyl acrylate, ethyl methacrylate, propyl acrylate, propyl methacrylate, butyl acrylate, butyl methacrylate, isobutyl methacrylate, hexyl acrylate, hexyl methacrylate, glycidyl acrylate, glycidyl methacrylate, hydroxyethyl acrylate, hydroxyethyl methacrylate, hydroxypropyl acrylate, hydroxypropyl methacrylate, hydroxybutyl acrylate, hydroxybutyl methacrylate, chloroethyl acrylate, chloroethyl methacrylate, methoxyethyl acrylate, methoxyethyl methacrylate, methoxybutyl acrylate, methoxybutyl acrylate, ethoxyethyl acrylate, ethoxyethyl methacrylate, furfuryl acrylate, furfuryl methacrylate, tetrahydrofuryl acrylate, tetrahydrofurfuryl methacrylate, vinyl acrylate, and vinyl methacrylate.

Non-limiting examples of di-, or polymethacrylates and acrylates used in formulations according to this invention are: ethylene, diethylene, polyethylene and other mono-, di-, or higher polyalkylene glycol dimethacrylates and diacrylates; $C_2$ to $C_{12}$ alkylene dimethacrylates and acrylates; trimethylolopropane trimethacrylate and acrylate; pentaerythritol trimethacrylate and acrylate; pentaerythritol tetramethacrylate and acrylate; 2,2-bis[4',4"-(3'"-methacroyl (or acroyl)-2'"-hydroxy-propoxy)phenyl· propane (commonly called Bis-GMA), and its urethane derivatives, 2,2-bis[4',4"-(2'"-methacroyl (or acroyl)-ethoxy) phenyl] propane (commonly called EBA), 2,2-bis[4',4"-(methacroyl)-phenyl]-propane (commonly called BADM), etc. Specific diacrylates and methacrylates, in addition to those just mentioned, are ethylene glycol dimethacrylate, ethylene glycol diacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, propylene diacrylate, propylene dimethacrylate, trimethylene diacrylate, trimethylene dimethacrylate, tetramethylene diacrylate, tetramethylene dimethacrylate, hexamethylene diacrylate, hexamethylene dimethacrylate, decamethylene diacrylate, decamethylene dimethacrylate, dodecamethylene diacrylate, and dodecamethylene dimethacrylate.

Non-limiting examples of solvents, used individually or in mixtures, suitable for use in formulations according to this invention are: Water, $C_1$–$C_5$ alcohols, ethylene chloride, dichloromethane, trichloroethylene, chloroform, $C_1$–$C_6$ alkylacetates, propionates and butyrates, acetone and other $C_1$–$C_4$ alkyl ketones, lower ($C_1$–$C_4$) ethers, etc. Specific examples of such solvents, in addition to those mentioned above, are methyl alcohol ethyl alcohol, propyl alcohol, isopropyl alcohol, butyl alcohol, sec. butyl alcohol, amyl alcohol, methyl acetate, ethyl acetate propyl acetate, isopropyl acetate, butyl acetate, amyl acetate, hexyl acetate, methyl propionate, ethyl propionate, butyl propionate, methyl butyrate, ethyl butyrate, methylethyl ketone, diethyl ketone, methyl butyl ketone, dimethyl ether, diethyl ether, methyl ethyl ether, dipropyl ether, dibutyl ether, ethyl butyl ether.

Any chemical dental composite restorative may be used in conjunction with the above-described primers. The restorative may be chemically or light cured, the preference of one over another depending on the particular formulation of the primer used, and especially on its curing system. For best results, the light cured primer should be used with light cured restoratives, and the chemically cured primers with chemically cured restoratives.

As indicated above, the restoratives are normally acrylic or methacrylic resins. Usually, they are based on polyethylenically unsaturated acrylates such as Bis-GMA and/or triethylene glycol dimethacrylate (TEGDM). There can be used any of the polyunsaturated acrylates or methacrylates mentioned above in the restorative or any of those set forth in the aforementioned Bowen, Lee, and Waknine patents. The restorative can also contain any of the conventional fillers, e.g., silica, glass, e.g., borosilicate glass, barium silicate, calcium silicate.

A typical procedure for restoring deficient veneers on cast restorations, according to this invention, involves the following steps:

1. (Optional): The damaged or worn out surface, e.g, on a crown, bridge, or denture, is roughened with a dental burr or abrasive disks or cones, to increase surface contact with the primer. The veneer surrounding the exposed metal is ground to a feather edge.
2. The area to be restored is coated with a thin layer of the primer having a chemical composition as described above. If the primer formulation contains a volatile solvent, the solvent is allowed to evaporate. The rate of evaporation of the solvent may be accelerated by blowing (preferably warm) air over the surface. If the primer is of the chemically cured type, sufficient time should be allowed to accomplish its cure. If it is of a light cured type, it may require irradiation with an appropriate instrument or it may be cured simultaneously with the light cured restorative applied thereafter.
3. A restorative material, perferably a composite restorative having a fluid or semi-fluid consistency, is applied over the primer, smoothed with a brush or spatula and/or covered with a thin foil (transparent or transluscent if the material is of the light cured type). If the restorative is chemically cured, it should be allowed enough time to achieve virtually full cure before finishing (usually three to five minutes). If it is light cured, it should be irriatiated for a period of time specified for the given material and light source (usually 10 seconds to 2 minutes).

4. (Optional): The restoration, after removing the foil (if used), is finished using conventional dental finishing tools and materials, such as carbide, corundum or diamond burrs, disks and cones, corundum and diamond polishing pastes, etc.

There can be employed conventional chemical curing agents and polymerization activators with the primers of the present invention. Thus, there can be employed a visible light activated polymerization initiators the $\alpha$-$\beta$ diketone type such as benzil, dl-camphoroquinone (2,3-bornanedione), and the like or benzoin and its derivatives (for example, benzoin alkyl ethers) in the case of ultraviolet cured formulations. Polymerization accelerators are employed in conjunction with such initiators. These accelerators are generally tertiary amines such as diethylaminoethyl acrylate, diethylamino ethylmethacrylate (commonly referred to as "DEAEMA"), dimethylamino ethylmethacrylate, and the like. Other accelerators include methacroyl or acroyl alkyl-dialkyl or dihydroxyalkyl amines and trialkylamines, having, preferably, one to ten carbon atoms in the alkyl moieties. Examples of such amines are tributylamine, tripropylamine, tridecylamine, butyl diethanoloamine, methyl, ethyl, propyl or butyl diethanoloamine, butyl dimethylamine, methacroylethyl-dimethylamine and cyclohexyl diethanoloamine.

A preferred class of polymerization initiators or activators for self cured primer formulations includes tertiary N-dialkyl substituted aromatic amines and aromatic peroxides (e.g., benzoyl peroxide).

The invention is further illustrated by examples. These examples are provided solely for better understanding the nature of this invention and should not be interpreted as limiting its scope.

DETAILED DESCRIPTION

Example 1

A chipped porcelain veneer on Degussa G Ceramic Gold had about nine square millimeters area of metal exposed. The veneer around the metal was ground down to a feature edge with a burr. The same burr was used to roughen the exposed surface. The area to be restored was thoroughly washed and dryed. A metal primer, having the following chemical composition, was applied with a brush:

| Compound | Parts (Weight) |
|---|---|
| Chloroform | 100 |
| Ethyl Acetate | 18 |
| Copolymer of acrylic acid with ethylmethacrylate having a molecular weight of about 200,000 and an acid No. of 100 | 12 |
| BIS-GMA | 3 |
| Triethylene Glycol Dimethacrylate | 2 |
| Camphoroquinone | 0.015 |
| methacroylethyl-dimethylamine | 0.02 |

The solvent was allowed to evaporate for two minutes. A paint-on type restorative material having a shade very similar to the shade of the surrounding veneer was applied over the area to be restored with a brush.

The restorative material included 40 parts polymerizable material (70% bis GMA and 30% triethylene glycol dimethacrylate) and 60 parts of filler (50 parts borosilicate glass and 10 parts silica). There was also included 0.3% benzil, 0.6% methacroylethyl dimethylamine and 0.03% butylated hydroxy toluene based on the total of polymerizable material and filler. The restoration was covered with a transparent polyester film, and was cured with a dental curing light (Optilux by Demetron Corporation) for 20 seconds. The foil was removed, and the restoration was finished with a diamond burr, followed by polishing with a composite polishing paste (Luster by Scientific Pharmaceuticals). The result was, esthetically and funtionally satisfactory.

Example 2

A chipped porcelain veneer on silver/palladium alloy was repaired using the same technique and primer as described in Example 1. As restorative, Silux (a dimethacrylate type filled resin manufactured by 3M Company) was used. It was opacified with titanium dioxide for better hiding of the metal background. The result was esthetically and functionally satisfactory.

Example 3

A worn acrylic veneer on Ceramco-brand nonprecious metal base was successfully restored using the same technique as described in Example 1, however, with the primer consisting of an alcohol/water solution of 3 parts of polyacrylic acid having a molecular weight of 750,000 and one part of hydroxethylmethacrylate with 0.2% of benzil and 0.3% of methacryoylethyl-dimethylamine used as polymerization activators. There was used CuRay Fil Restorative System (manufactured by Scientific Pharmaceuticals) as a restorative. The result was esthetically and functionally satisfactory.

Example 4

The adhesive strength obtained with a primer formulation described in Example 1 was determined in in-vitro studies performed as follows:

Alloys, listed in the Table below, were cast into a 1×1 cm square specimen 2 mm thick. The specimens were embedded in phenolic rings with an epoxy resin and placed in special holders, adapted to attachment to an adhesion tester. The alloy surface was roughened with 320 grit silicon-carbide abrasive to produce a uniform surface roughness reading of 0.35±3 mm on a Surftester III (Mitutoyo, Japan). After roughening, the specimen was washed with water and dried. The primer was applied with a brush over the roughened area and dried at 37° C. for 2 minutes. Cylindrical specimen made of the same restorative as in Example 1 5 mm in diameter was cured directly over the primed metal surfaces, using a Teflon split mold. Five samples were prepared for each alloy.

Adhesion was tested under sheer forces on a Richie Universal Tester, at a crosshead speed of 1 mm per minute. The results are presented in the Table below:

| Metal | Average Adhesive Strength | |
| --- | --- | --- |
| | PSI | MPA |
| Degussa G-Ceramic Gold | 867 | 5.8 |
| Ceramco-Non Precious Alloy | 785 | 5.3 |
| Olympia - by Jelenko | 705 | 4.8 |
| Albabond - Silver Palladium Alloy | 840 | 5.7 |

The results obtained in parallel tests, with no primer or with functional organosilane primer based on methacroylpropyl trimethoxy silane (Scientific Pharmaceuticals' Porcelain Primer) have shown adhesive strength in the range of 100–300 psi on gold and gold alloys, and 250–550 psi on Albabond Silver/Palladium Alloy and Ceramco Non-Precious Alloy.

What is claimed is:

1. A method of repairing a damaged, worn or otherwise deficient veneer on dental prosthesis comprising application over the metal base in the area to be restored a polymerizable primer composition containing (a) (1) acrylic acid, methacrylic acid, polyacrylic acid, or polymethacrylic acid and (2) an ester of acrylic acid, an ester of methacrylic acid, a polymer of an ester of acrylic acid or a polymer of an ester of methacrylic acid, or (b) a copolymer of either acrylic acid or methacrylic acid with an ester of acrylic acid or an ester of methacrylic acid, or (c) a copolymer as in (b) together with an ester of acrylic acid or an ester of methacrylic acid.

2. A method according to claim 1 wherein the composition on a solvent free basis has an acid number of at least 20.

3. A method according to claim 2 wherein the acid number is above 65.

4. A method according to claim 3 wherein the acid number is 80 to 120.

5. A method according to claim 1 including the additional step of applying over the area to be restored a curable dental restorative material and curing the restorative material.

6. A method according to claim 2 including the additional step of applying over the area to be restored a curable dental restorative material and curing the restorative material.

7. A method according to claim 5 in which the surface to be restored is shaped or roughened with dental abrasives.

8. A method according to claim 5 in which the primer composition contains polyacrylic or polymethacrylic acid having an average molecular weight of 2000 to 1,000,000 and an acrylate or methacrylate ester having at least 1 hydroxy group per molecule.

9. A method according to claim 8 in which the ester is a hydroxy $(C_1-C_5)$ alkylacrylate or methacrylate.

10. A method according to claim 5 in which the copolymer is a copolymer of methacrylic or acrylic acid with a substituted, or unsubstituted phenyl, cyclohexyl, $(C_1-C_6)$ alkyl, glycidyl, hydroxy-$(C_2-C_4)$ alkyl, $(C_1-C_6)$ chloroalkyl, $(C_1-C_4)$ alkoxyalkyl, tetrahydrofurfuryl vinyl acrylate or methacrylate.

11. A method according to claim 5 in which the primer formulation also contains a mono-, di-, or higher polyacrylate or methacrylate ester.

12. A method according to claim 11 in which such monoacrylate or methacrylate esters is a $(C_1-C_6)$ alkyl, cyclohexyl, tetrahydrofurfuryl, alkoxyalkyl $(C_1-C_4)$, hydroxy-$(C_1-C_4)$ alkyl, vinyl or phenyl acrylate or methacrylate.

13. A method according to claim 11 including a di- or higher poly-acrylate or methacrylate ester are selected from the group consisting of: mono-, di-, tri-, tetra-, penta-, and hexa- ethylene glycol dimethacrylates or acrylates; $(C_1-C_8)$ alkylene diol- dimethacrylates, BIS-GMA, its substituted derivatives and acrylate analogs; EBA, its substituted derivatives and acrylate analogs; BADM, its substituted derivatives and acrylate analogs; pentaerythritol di-, tri- and tetra- acrylate or methacrylate and trimethylolopropane di- or triacrylate or methacrylate.

14. A method according to claim 1 in which a solvent is used as a carrier for the primer composition consisting essentially of water, a $(C_1-C_5)$ alkyl alcohol, $(C_1-C_4)$ alkyl acetates or a mixture thereof.

15. A method according to claim 5 in which a solvent is used as a carrier for the primer composition consisting essentially of water, a $(C_1-C_5)$ alkyl alcohol, $(C_1-C_4)$ alkyl acetates or a mixture thereof.

16. A mthod according to claim 8 in which a solvent is used as a carrier for the primer composition consisting essentially of water, a $(C_1-C_5)$ alkyl alcohol, $(C_1-C_4)$ alkyl acetates or a mixture thereof.

17. A method according to claim 1 in which a solvent is used as a carrier for the primer composition consisting essentially of methylene chloride, chloroform, ethylene chloride, a $(C_1-C_6)$ alkyl acetate, acetone, ethyl ether or mixture thereof.

18. A method according to claim 5 in which a solvent is used as a carrier for the primer compostion consisting essentially of methylene chloride, chloroform, ethylene chloride, a $(C_1-C_6)$ alkyl acetate, acetone, ethyl ether or mixture thereof.

19. A method according to claim 8 in which a solvent is used as a carrier for the primer composition consisting essentially of methylene chloride, chloroform, ethylene chloride, a $(C_1-C_6)$ alkyl acetate, acetone, ethyl ether or mixture thereof.

20. A method according to claim 10 in which a solvent is used as a carrier for the primer composition consisting essentially of methylene chloride, chloroform, ethylene chloride, a $(C_1-C_6)$ alkyl acetate, acetone, ethyl ether or mixture thereof.

21. A method according to claim 5 wherein a chemically or light polymerizable acrylate or methacrylate restorative is employed over the primer as a final coating.

* * * * *